US008206695B2

United States Patent
Lin

(10) Patent No.: US 8,206,695 B2
(45) Date of Patent: Jun. 26, 2012

(54) EYELASH ENHANCEMENT COMPOSITION AND METHOD OF TREATMENT

(75) Inventor: Suan Lin, San Mateo, CA (US)

(73) Assignee: La Canada Ventures, Inc., San Mateo, CA (US)

( * ) Notice: Subject to any disclaimer, the term of this patent is extended or adjusted under 35 U.S.C. 154(b) by 1231 days.

(21) Appl. No.: 11/870,257

(22) Filed: Oct. 10, 2007

(65) Prior Publication Data

US 2008/0269332 A1    Oct. 30, 2008

Related U.S. Application Data

(60) Provisional application No. 60/914,259, filed on Apr. 26, 2007.

(51) Int. Cl.
*A61Q 1/10* (2006.01)
(52) U.S. Cl. .................................. 424/70.7; 514/622
(58) Field of Classification Search ................ None
See application file for complete search history.

(56) References Cited

U.S. PATENT DOCUMENTS 7,351,404 B2 * 4/2008 Woodward et al. .......... 424/70.1
2007/0160562 A1 * 7/2007 Brinkenhoff ............... 424/70.22

* cited by examiner

*Primary Examiner* — Jyothsna Venkat
(74) *Attorney, Agent, or Firm* — Wayne W. Montgomery

(57) ABSTRACT

Effective enhancement of eyelash length and density can be obtained by topical applications of an active agent selected from a class of compounds consisting of synthetic prostaglandin agonists, polymers thereof and mixtures thereof preferably having the chemical formula of $C_{24}H_{35}NO_5$, such as 7-[3.5-dihydroxy-2-(3-hydroxy-4phenoxy-but-1-enyl)-cyclopentyl]-hept-5-enoic acid ethylamide. Such active agents having a molecular weight of 417.54 can be employed in concentrations from 0.00075% to 0.03% by weight in mixtures with inactive ingredients, such as gels, oils, etc. Results are obtained by daily topical applications of active agent in such liquid mixtures (tinctures) at the roots of the lashes and/or lash follicles.

3 Claims, No Drawings

EYELASH ENHANCEMENT COMPOSITION AND METHOD OF TREATMENT

This application claims priority from U.S. Provisional Application, entitled "EYELASH ENHANCEMENT COMPOSITION AND METHOD OF TREATMENT" Ser. No. 60/914,259 and filed on May 11, 2007.

BACKGROUND OF THE INVENTION

Field of the Invention

The present invention relates to compositions and methods for enhancement of eyelash growth, in particular promoting lash growth, length and density. The new composition is also effective in reducing and/or preventing eyelash fallout during chemotherapy and promoting lash/eyebrow growth in the skin condition of alopecia areata.

A desire for longer, thicker lashes by women is apparent by the abundance of cosmetic products that aim to temporarily alter the appearance of the user, i.e. mascara, lash extensions. Most of such products produce only temporary results, lasting a few hours to a few weeks. Eyelash transplants have been successful in producing longer lasting results but the costs of transplantations are often very prohibitive to the general public.

Recently a new class of synthetic prostaglandin analogues has been proposed for eyelash enhancement, see for example U.S. Patent Application No. 20030147823 published Aug. 7, 2003 for "stimulating hair growth in eyelashes". These compounds have abundant safety data for usage in intraocular in treatment of glaucoma but lack rigorous studies on usage for topical applications to improve appearance of eyelashes.

Other compositions have been touted for enhancing hair growth, such as U.S. Pat. No. 4,874,761 for hair growing agent with aliphatic carboxylic acid and U.S. Pat. No. 4,769,231 for a hair tonic extract from dong chong xia cao. Likewise U.S. Pat. No. 4,853,216 teaches the topical application of compositions containing an alpha adrenergic agonist and U.S. Letters Patent No. 4,656,192 discloses tropolone ester as antimicrobial agent, hair growth stimulant.

Also some prior compositions include bimataprost and latanoprost (used in Jan Marini Lash Conditioner and Revitalash®).

Some of the prior compositions mentioned have resulted in eye irritation and in rare side effects such as a darkening of surrounding skin or iris, when applied to a user's eyelashes.

It is an object of the this invention to provide a new composition which has an active agent different than the above mentioned compounds suitable for both male and female users which is effective for eyelash enhancement as disclosed herein.

It is also an object to provide a new composition for enhancement of eyelashes which can safely be used by contact lens wearers, and persons with very sensitive eyes.

A further object is the provision of a topical mixture having the active agent disclosed herein which is more effective than the prior art products.

It also an object to provide a mixture with the active agent disclosed herein that counteracts the loss of eyelashes during chemotherapy treatment for cancer or chronic inflammatory diseases which also stunt lash growth.

A specific object is to avoid the loss of eyelash growth in patients treated methotrexate for Lupus which can result in a perceived significant social stigma.

It is also an object to overcome the existence of the thin, brittle, short lashes resulting from chemotherapy due to the advent of new medical techniques.

Another object is to avoid painful injections of steroids into eyelash lash beds to preserve lash growth and stabilization.

SUMMARY OF INVENTION

The above objects can be accomplished by using, as an active agent, a compound selected from class consisting of synthetic prostaglandin agonists, polymers thereof and mixtures thereof and more preferably compounds having the formula of $C_{24}H_{35}NO_5$, such as 7-[3.5-dihydroxy-2-(3-hydroxy-4-phenoxy-but-1-enyl)-cyclopentyl]-hept-5-enoic acid ethylamide, for topical application to the eyelash base (follicles) to improve eyelash and eyebrow, length, growth and density. These active agents (compounds) are mixed with inert, hypoallergenic ingredients, such as solvents, recipients, cosmetic bases and gels, to form a liquid mixture which contains from 0.00075% to 0.03% by weight of the active agent.

The method of use includes topical applications of the liquid mixture with the active agent to the eyelash base (follicles) on a daily basis by wetting the base or roots of the eyelashes with the liquid mixture until the desired result is achieved. The liquid mixture is topically applied to the base of the eye lashes. Typically 0.2 cc of the liquid mixture is sufficient for daily usage for both eyelashes over a 6 month period. Thus the daily recommended usage is approximately 0.001 cc for both lash bases.

DESCRIPTION OF THE INVENTION

A more complete appreciation of the invention and many of the attendant advantages thereof will be readily obtained by reference to the following description. Also a wide variety of uses is contemplated by present invention and is to be understood that the active agents can be utilized in different treatments depending on conditions perceived at the time they are used. Active agents, are compounds selected from class of compounds consisting of synthetic prostaglandin agonists, polymers thereof and mixtures thereof and more preferably compounds having the chemical formula of $C_{24}H_{35}NO_5$, such as 7-[3.5-dihydroxy-2-(3-hydroxy-4-phenoxy-but-1-enyl)-cyclopentyl]-hept-5-enoic acid ethylamide or (z)-7-((1R,2R,3R,5S)-3,5-dihydroxy-2-((R,E)-3-hydroxy-4-phenoxybut-1-enyl)cyclopentyl)-N-ethylhept-5-enamide.

The molecular weight of the latter is 417.54 and the structural formula is:

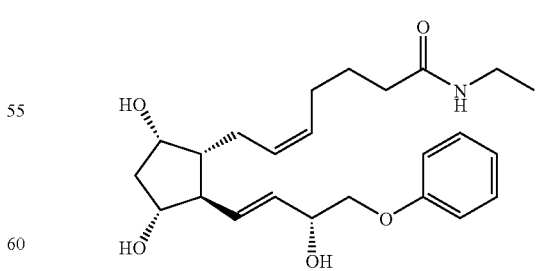

Generally, it is preferred that the active agents in a liquid mixture contain no more than 0.03% by weight of the active agent. However treatment according to the present invention may include a very wide effective concentration range of the active agents depending the specific therapeutic goal desired.

Notwithstanding, the active agents can have concentrations from 0.0075 to 0.03% by weight in liquid mixtures with inert ingredients.

The inert ingredients can include a carrier, solvent, recipient, cosmetic base or gelling agent. Preferably, these components are hypoallergenic and cause minimal irritation to surrounding eyes. Suitable carriers, solvents, recipients, cosmetic bases and gels are well known in the art. Any formulation which allows delivery of the active agents of the present invention to the hair, hair follicles are suitable for use in the present invention.

Suitable solvents include alkyl esters of fatty acids, preferably $C_{1-12}$, more preferably $C_{3-10}$, alkyl esters of saturated or unsaturated fatty acids containing 8-22 carbon atoms. Preferred solvents, include sodium lactate, sodium PCA, sorbitol and praline (Prodew 300), etc. Alcohols such as ethanol, propanol, isopropanol, propylene glycol, etc., as well as aqueous mixtures of these alcohols may also are suitable.

In a preferred embodiment, the active compounds is 7-[3,5-dihydroxy-2-(3-hydroxy-4-phenoxy-but-1-enyl)-cyclopentyl]-hept-5-enoic acid ethylamide or (z)-7-((1R,2R,3R,5S)-3,5-dihydroxy-2-((R,E)-3-hydroxy-4-phenoxybut-1-enyl)cyclopentyl)-N-ethylhept-5-enamide. The ratio of active agent to solvent can vary widely but normally will not exceed 0.03% by weight of the resulting mixture with inert ingredients. The resulting liquid mixture is typically referred to as "tincture" which herein means a solution of the active agents in a solvent.

If desired, a known gelling agent may be added to the liquid mixture of inert ingredients. Suitable gelling agents include synthetic high molecular weight cross linked polymers of acrylic acid, more specifically an acrylate/$C_{10-30}$ alkyl acrylate copolymer available under the trade name Carbopol Ultrez 20 sold by Noveon Inc. of Lubrizol Corporation. Other suitable gelling agents include cellulose and cellulose derivatives such as dihydroxyethyl cellulose (ULTRAGEL® sold by Johnson & Johnson). Whereas the ULTRAGEL contains mostly water, the CARBOMER 1342 was used in a ratio of about 0.5-1.0 percent by weight with the remainder of the gelling agent being purified water.

The forgoing ingredients make up what is commonly referred to as a cosmetically acceptable vehicle, such as those disclosed in U.S. Pat. No. 6,821,524 and herein.

To practice the method requires a topical application to the base of lash follicles of a host in need thereof. Tests conducted for the invention included only such external, topical treatments. Internal treatment is not contemplated by the invention.

As to the frequency of application, it is contemplated that the active agent, in an inert mixture, in the form of gel, be applied nightly using an eyeliner brush to the base of upper eyelash follicles. Additional daily applications are discouraged. Once desired appearance has been reached, the application frequency is reduced to every other day for maintenance.

The active agents described and method of treatment disclosed, has been proven to be very effective in producing longer and thicker lash growth.

EXAMPLES

A randomized double blind clinical trial was performed on 34 healthy volunteers to assess the eyelash growth properties of the novel product, a synthetic topical prostaglandin analogue, having the structural formula of (z)-7-((1R,2R,3R,5S)-3,5-dihydroxy-2-((R,E)-3 hydroxy-4-phenoxybut-1-enyl) cyclopentyl)-hept-5-enoic acid ethylamide.

A placebo solution of the following ingredients was prepared:

List of Ingredients and Corresponding Percentages by weight:

| INGREDIENTS | PERCENTAGE |
| --- | --- |
| Purified Water | 95.886 |
| Hydrolyzed Glycosaminoglycan | 0.750 |
| Phenoxyethanol | 0.540 |
| Triethanolamine | 0.520 |
| Acrylates C10-30 Alkyl Acrylate Crosspolymer | 0.500 |
| C12-15 Alkyl Benzoate | 0.500 |
| Caprylyl Glycol | 0.430 |
| Panthenol | 0.250 |
| Sodium Chloride | 0.130 |
| Biotin | 0.100 |
| Sodium Lactate | 0.087 |
| Sodium PCA | 0.032 |
| Ethanol | 0.030 |
| Active | 0.030 |
| Sorbitol | 0.023 |
| Proline | 0.009 |

Using this mixture as the placebo, three separate solutions with the active agent were created from three separate portions of this mixture, identified as the solutions below:

Solution A having 0.03% by weight of (z)-7-((1R,2R,3R,5S)-3,5-dihydroxy-2-((R,E)-3 hydroxy-4-phenoxybut-1-enyl) cyclopentyl)-hept-5-enoic acid ethylamide as the active agent.

Solution B having 0.015% by weight of (z)-7-((1R,2R,3R,5S)-3,5-dihydroxy-2-((R,E)-3 hydroxy-4-phenoxybut-1-enyl)cyclopentyl)-hept-5-enoic acid ethylamide as the active agent.

Solution D 0.0075% by weight of (z)-7-((1R,2R,3R,5S)-3,5-dihydroxy-2-((R,E)-3 hydroxy-4-phenoxybut-1-enyl)cyclopentyl)-hept-5-enoic acid ethylamide as the active agent.

Solution C being the placebo mixture, described above.

These solutions were each applied daily to the roots of the upper right and left eyelashes of the patients in a quantity of approximately 0.0164 ml. Patients applied the eyelash product daily for 4 weeks on the root of the upper eyelashes only since some of the solution used may ultimately be deposited on the lower lash interfering with the studies' parameters.

Methods: 34 patients were randomly assigned to one of three different treatment groups based on a standard treatment of the upper right lash and different treatments of the upper left eye lash with varying concentrations of the active product and a placebo.

Age range of the patients was 20-56; 33 female, 1 male. Three different treatment Groups were constructed based on RIGHT EYE lash treatment/LEFT EYE lash treatment and defined as Groups A/B, A/D and A/C). All patients used Solution A on the right eye lash which is the "Control Group", with Solutions B, D, and C used on the left eye lash of these same patients.

Group A/B (14 patients) used Solution A on the upper right lash and Solution B on the upper left lash.

Group A/D (9 patients) used Solution A on the upper right lash and Solution D on the upper left lash.

Group A/C (11 patients) used Solution A on the upper right lash and the placebo, Solution C, on the upper left lash.

| Group A/B | | Group A/C | | Group A/D | |
|---|---|---|---|---|---|
| Right Eye | Left Eye | Right eye | Left Eye | Right Eye | Left Eye |
| Solution A | Solution B | Solution A | Solution C | Solution A | Solution D |

Using the right and left eyelash of the same patient for the study eliminated variables based on the individual characteristics.

Eyelash Measurements

After four (4) weeks upper RIGHT eyelash measurement were made for all 34 randomized patients. The upper LEFT eyelash measurement were made for the 14 patients using Solution B, for the 9 patients using Solution D and the 11 patients using Solution C (the placebo).

Eyelash measurements for both the upper right and left eyelashes were taken in the medial, middle and lateral locations on both upper and lower eyelids using micocalipers and measured to 0.1 mm. The mean of the six measurements were then used to calculate the eyelash length for each eye. Measurements were taken at the initiation of the study to use as standard base.

The technicians performing the measurements were blinded to the patient group assignment. A paired two-tailed Student's t-Test was used for statistical analysis. All patients enrolled into the study underwent a standard informed consent procedure.

Results: All treatment groups, except the patients using the placebo on the left eye lash, demonstrated a statistically significant growth in eyelash length after 4 weeks of daily use. There were no complications, 19 patients reported minimal initial transient irritation.

Right eyelash growth of 34 patients using Solution A thereon was 1.69 mm

Left eyelash growth of 14 patients using Solution B thereon was 1.94 mm

Left eyelash growth of 9 patients using Solution D thereon was 1.44 mm

Left eyelash growth of 11 patients using Solution C thereon was 0.63 mm 19 patients (56%, 19/34) reported mild or minimal irritation with use of the product. This typically resolved after several days of use. One patient reported moderate irritation and discontinued the product. 9 patients (26%, 9/34) subjectively reported an increase in the thickness or fullness of their eyelashes with use of the product.

Averaging the growth data using the current active agent and the normal growth using the placebo, the increase lash growth is 1.69/0.63×100=268.25%. Moreover, the mid concentration of the active agent, Solution B, demonstrated even better results, 307%.

Modifications and additions to those set forth specifically above are possible within the scope of the present invention.

What is claimed as new and is desired to be secured by Letters Patent of the United States is:

1. An eyelash enhancement composition wherein the active agent is (z)-7-((1R,2R,3R,5S)-3,5-dihydroxy-2-(R,E)-3-hydroxy-4-phenoxy-but-1-enyl)-cyclopentyl)-hept-5-enamide where in the active agent is present by weight in concentration of about 0.015% by weight.

2. An eyelash enhancement composition according to claim 1 where in the active agent is present in an at least 95% by weight purified water base.

3. An eyelash enhancement composition defined in claim 2 where in the purified water base includes at least one inert ingredient selected from the group consisting of Hydrolyzed Glycosaminoglycan, Phenoxyethanol, Triethanolamine, Acrylates C 10-30 Alkyl Acrylate Crosspolymer, C12-15 Alkyl Benzoate, Caprylyl Glycol, Panthenol, Sodium Chloride, Biotin, Sodium Lactate, Sodium PCA, Ethanol, Sorbitol and Proline.

* * * * *